United States Patent [19]

Spry

[11] 4,334,064
[45] Jun. 8, 1982

[54] CEPHALOSPORIN VINYL HALIDES

[75] Inventor: Douglas O. Spry, Indianapolis, Ind.

[73] Assignee: Eli Lilly and Company, Indianapolis, Ind.

[21] Appl. No.: 249,056

[22] Filed: Mar. 30, 1981

Related U.S. Application Data

[62] Division of Ser. No. 91,603, Nov. 5, 1979, Pat. No. 4,299,954.

[51] Int. Cl.$^3$ ............................................ C07D 501/18
[52] U.S. Cl. ..................................... 544/30; 424/246; 544/28
[58] Field of Search ....................... 544/28, 30, 21, 27, 544/16

[56] References Cited

U.S. PATENT DOCUMENTS

| | | | |
|---|---|---|---|
| 3,578,660 | 5/1971 | Cooper | 544/30 |
| 3,660,396 | 5/1972 | Wright | 544/30 |
| 3,852,282 | 12/1974 | Dolfini | 544/30 |
| 3,923,795 | 12/1975 | Spry | 544/30 |
| 3,933,806 | 1/1976 | Spry | 544/30 |
| 3,963,712 | 6/1976 | Koyama | 544/30 |
| 4,098,999 | 7/1978 | Dolfini | 544/30 |

OTHER PUBLICATIONS

Wright et al., J. Med. Chem. 14 420–425 (1971).
Kaiser et al., J. Med. Chem. 14 426–429 (1971).

*Primary Examiner*—Nicholas S. Rizzo
*Attorney, Agent, or Firm*—William B. Scanlon; Arthur R. Whale

[57] ABSTRACT

7-Acylamido-2-halomethylidene-3-methyl and 3-acetoxymethyl-3-cephem-4-carboxylic acids and esters are prepared via reaction of the corresponding 2-exomethylene-3-cephem ester sulfoxides with chloro (or bromo) dimethyliminium chlorides (or bromides). The 2-halomethylidene derivatives are useful as antimicrobial agents and intermediates to novel 2-acyloxymethylidene cephalosporins and to the known 2-aryl (or alkyl) mercaptomethylidene cephalosporins.

1 Claim, No Drawings

CEPHALOSPORIN VINYL HALIDES

This application is a division of application Ser. No. 91,603, filed Nov. 5, 1979 now U.S. Pat. No. 4,299,954.

BACKGROUND OF THE INVENTION

This invention relates to cephalosporin antibiotic compounds. In particular, it relates to cephalosporin compounds substituted in the 2-position with a vinyl halide group referred to herein as a 2-halomethylidene group.

Cephalosporins substituted in the 2-position of the six-membered dihydrothiazine ring have been previously described. 2-Methyl and 2-methylenecephalosporin compounds are described by I. G. Wright et al., *J. Med. Chem.* 1971, 14, 420–425. G. V. Kaiser, et al. ibid 426–429, describe 2-thiomethyl and 2-thiomethylene cephalosporin compounds which are obtained by the addition of mercaptans to the 2-exomethylenecephalosporin sulfoxides described by Wright. Dolfini, U.S. Pat. No. 3,852,282, teaches cephalosporins substituted in the 2-position by halogen, lower alkoxy, lower alkenyloxy, lower alkynyloxy, aryloxy, lower alkanoyloxy, lower alkylthio, lower alkenylthio, lower alkynylthio, arylthio, aroylthia or alkanoylthia.

DETAILED DESCRIPTION

This invention relates to 2-halomethylidene cephalosporin compounds represented by the following structural formula 1.

wherein R is hydrogen or an acyl group $$R'-\overset{O}{\underset{\|}{C}}-$$

wherein R' is $C_1$–$C_4$ alkyl, cyanomethyl, halomethyl, phenyl; a group of the formula wherein a and a' are independently hydrogen, halogen, $C_1$–$C_4$ alkyl, $C_1$–$C_4$ alkoxy, or nitro; Z is O or S, and m is 0 or 1; a group of the formula $$R''-\underset{W}{\overset{|}{C}H}-$$

wherein R" is cyclohexenyl, 1,4-cyclohexadienyl, a phenyl or substituted phenyl group of the formula wherein a and a' have the same meanings as defined above, or R" is thienyl or furyl; W is amino, protected-amino, hydroxy, protected-hydroxy, carboxy or protected-carboxy; or R' is a heteroarylmethyl group of the formula $$R'''-CH_2-$$

wherein R''' is selected from the group consisting of wherein
each b is hydrogen, $C_1$–$C_4$ alkyl or amino, and each b' is hydrogen or $C_1$–$C_4$ alkyl;
$R_1$ is hydrogen or acetoxy;
X is chloro or bromo;
$R_2$ is hydrogen or a carboxylic acid protecting group; and n is 0 or 1.

In the above formula 1, the term $C_1$–$C_4$ alkyl refers to methyl, ethyl, n-propyl, iso-propyl, n-butyl, iso-butyl, sec-butyl and t-butyl; halomethyl refers to chloromethyl, bromomethyl, or iodomethyl; $C_1$–$C_4$ alkoxy refers to methoxy, ethoxy, n-propoxy, iso-propoxy, n-butoxy and like lower alkyl ether groups; and the term halogen refers to fluoro, chloro and bromo.

The term carboxylic acid protecting group refers to the commonly used ester derivatives of carboxylic acid groups of cephalosporin compounds. These ester groups function to protect or block the acidic carboxylic acid function while reactions at other sites in the molecule are carried out. Numerous ester groups which serve this function are recognized in the art and include such esters as benzyl, p-nitrobenzyl, p-methoxybenzyl, diphenylmethyl, triphenylmethyl, the haloalkyl esters for example, iodomethyl, 2,2,2-trichloroethyl, and 2,2,2-tribromoethyl; and phenacyl and substituted phenacyl such as nitrophenacyl.

The term protected-carboxy has reference to the same carboxylic acid protecting ester groups described above.

The term protected-amino refers to the amino group substituted with one of the commonly used amino blocking groups. These groups serve to block or protect the basic amino group while reactions at other sites in the molecule are carried out. Examples of such groups well recognized in the art include the aryl and alkyl urethane forming groups such as t-butyloxycarbonyl, trichloroethoxycarbonyl, benzyloxycarbonyl, p-nitrobenzyloxycarbonyl, cyclopentyloxycarbonyl and like groups; the enamines formed with active methylene compounds such as acetyl acetone, methyl acetoacetate and the like; and the arylmethyl groups, for example, diphenylmethyl and triphenylmethyl.

The term protected-hydroxy refers herein to the recognized hydroxy protecting or blocking groups such as esters, for example, the formyl, acetyl, chloroacetyl and like esters; the ethers such as those formed with tetrahydropyran, and methylvinyl ether; the groups which form carbonate esters such as t-butyloxycarbonyl, trichloroethoxycarbonyl, benzyloxycarbonyl, p-nitrobenzyloxycarbonyl and the like.

The 2-chloro or 2-bromomethylidene cephalosporin esters of the above formula wherein n is 0 and R and $R_2$ are other than hydrogen are prepared by reacting a 2-exomethylene sulfoxide ester, prepared as described by Wright, et al. supra, in an inert solvent with preformed chloro or bromo dimethyl imminium chloride or bromide (Vilsmeier reagent). The Vilsmeier reagent is prepared in the usual manner by reacting phosphorus trichloride or phosphorus tribromide with dmethylformamide. The preparation of the 2-halomethylidene cephalosporin ester is illustrated in the following reaction scheme.

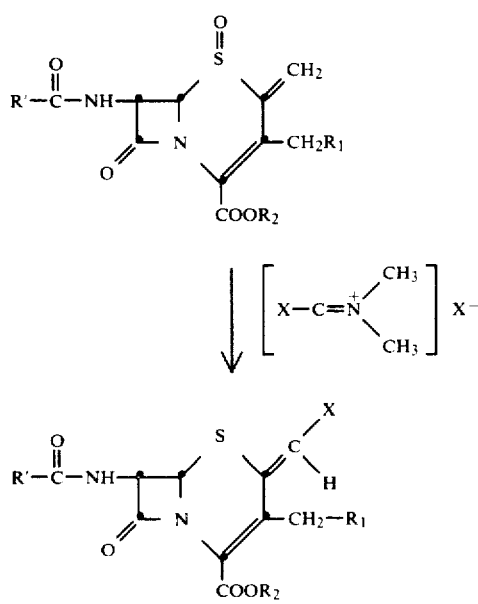

In the above reaction scheme, R, $R_1$, and X have the same meaning as defined in formula 1 and $R_2$ refers to a carboxylic acid ester group.

The Vilsmeier reagent (chloro or bromo dimethyliminium chloride or bromide) is prepared at about −70° to about −30° C. by adding phosphorus trichloride or phosphorus tribromide to an excess of dimethylformamide. After the Vilsmeier reagent has formed, the 2-exomethylenecephalosporin sulfoxide ester is added to the Vilsmeier reagent in excess dimethylformamide. Alternatively, the 2-exomethylene cephalosporin sulfoxide ester can be dissolved in an inert solvent and the pre-formed Vilsmeier reagent in DMF added to the solution.

Inert solvents which can be employed in the alternative mode of addition include the halogenated hydrocarbons such as methylene chloride, chloroform, chlorinated ethane solvents such as 2,2,2-trichloroethane or 1,1,2-trichloroethane and like halogenated hydrocarbon solvents.

It is preferred in carrying out the preparation of the compounds of this invention that excess DMF be employed in the preparation of the Vilsmeier reagent. Following the formation of the Vilsmeier reagent in the cold, a solution of the 2-exomethylene cephalosporin sulfoxide ester in DMF or other suitable inert solvent is added to the solution of the Vilsmeier reagent.

The preparation of the 2-halomethylidene cephalosporin esters is carried out at a temperature between about −70° C. to about 10° C.

The dimethylformamide used in the preparation of the Vilsmeier reagent and in the preparation of the 2-halomethylidene cephalosporins is dried before use. Drying over molecular sieve is a convenient method for obtaining dry DMF for use in the reactions.

In preparing the 2-halomethylidene cephalosporins, the ratio of the amount of Vilsmeier reagent to the 2-exomethylenecephalosporin sulfoxide is between about one and about two moles of reagent per mole of sulfoxide.

The 2-halomethylidene cephalosporin esters are recovered from the reaction mixture preferably by diluting the reaction mixture with an organic solvent such as ethyl acetate or amyl acetate, and thereafter washing the mixture with water to remove DMF and other water solubles. After drying the mixture and evaporation of the solution to dryness, the reaction product mixture is chromatographed over a suitable adsorbent such as silica gel to provide the product. The product can be purified by further chromatography, if needed.

In carrying out the preparation of a 2-halomethylidene compound any amino, carboxy or hydroxy groups in the 2-exomethylene sulfoxide starting material are protected beforehand to prevent untoward reaction with the Vilsmeier reagent. Following the reaction the protecting groups can be removed to provide the deprotected 2-halomethylidene cephalosporin free acid. Alternatively, the protecting groups can be left intact to protect such amino, hydroxy and carboxy groups with the 2-halomethylidene cephalosporin is used to prepare a 2-alkanoyloxymethylidene cephalosporin of the formula 2 as described hereinafter.

Illustrative of the 2-halomethylidene cephalosporins provided by the above-described reaction are:

2,2,2-trichloroethyl 7-acetamido-2-chloromethylidene-3-methyl-3-cephem-4-carboxylate, p-nitrobenzyl 7-phenoxyacetamido-2-chloromethylidene-3-methyl-3-cephem-4-carboxylate, p-nitrobenzyl 7-phenoxyacetamido-2-bromomethylidene-3-methyl-3-cephem-4-carboxylate, 2,2,2-trichloroethyl 7-propionamido-2-chloromethylidene-3-acetoxymethyl-3-cephem-4-carboxylate, p-nitrobenzyl 7-phenoxyacetamido-2-chloromethylidene-3-acetoxymethyl-3-cephem-4-carboxylate, p-methoxybenzyl 7-phenylacetamido-2-chloromethylidene-3-acetoxymethyl-3-cephem-4-carboxylate, diphenylmethyl 7-phenylacetamido-2-bromomethylidene-3-methyl-3-cephem-4-carboxylate, p-nitrobenzyl 7-(2-thienylacetamido)-2-chloromethylidene-3-acetoxymethyl-3-cephem-4-carboxylate, benzyl 7-(2-furylacetamido)-2-chloromethylidene-3-methyl-3-cephem-4-carboxylate, diphenylmethyl 7-benzamido-2-bromomethylidene-3-acetoxymethyl-3-cephem-4-carboxylate, p-nitrobenzyl 7-phenylmercaptoacetamido-2-bromomethylidene-3-methyl-3-cephem-4-carboxylate, p-methoxybenzyl 7-phenylmercaptoacetamido-2-chloromethylidene-3-acetoxymethyl-3-cephem-4-carboxylate, iodomethyl 7-benzamido-2-chloromethylidene-3-acetoxymethyl-3-cephem-4-carboxylate, t-butyl 7-(2-thienylacetamido)-2-chloromethylidene-3-acetoxymethyl-3-cephem-4-carboxylate.

diphenylmethyl 7-cyanoacetamido-2-chloromethylidene-3-acetoxymethyl-3-cephem-4-carboxylate, p-nitrobenzyl 7-bromoacetamido-2-bromomethylidene-3-acetoxymethyl-3-cephem-4-carboxylate, p-nitrobenzyl 7-[α-amino-α-(1,4-cyclohexadienyl)-acetamido]-2-chloromethylidene-3-methyl-3-cephem-4-carboxylate, p-nitrobenzyl 7-phenylglycylamido-2-chloromethylidene-3-methyl-3-cephem-4-carboxylate, p-nitrobenzyl 7-(α-t-butyloxycarbamido-α-phenylacetamido)-2-chloromethylidene-3-methyl-3-cephem-4-carboxylate, p-nitrobenzyl 7-(α-formyloxy-α-phenylacetamido)-2-chloromethylidene-3-acetoxymethyl-3-cephem-4-carboxylate, 2,2,2-trichloroethyl 7-mandelamido-2-bromomethylidene-3-acetoxymethyl-3-cephem-4-carboxylate, 2,2,2-trichloroethyl 7-(2-benzofurylacetamido)-2-chloromethylidene-3-acetoxymethyl-3-cephem-4-carboxylate, diphenylmethyl 7-[(2-amino-1,3-thiazol-5-yl)acetamido]-2-bromomethylidene-3-methyl-3-cephem-4-carboxylate, diphenylmethyl 7-[(2-methyl-1,3-thiazol-5-yl)acetamido]-2-chloromethylidene-3-methyl-3-cephem-4-carboxylate, p-methoxybenzyl 7-[(1,3,4-thiadiazol-2-yl)acetamido]-2-chloromethylidene-3-methyl-3-cephem-4-carboxylate, p-nitrobenzyl 7-[(1,3,4-oxadiazole-2-yl)acetamido]-2-bromomethylidene-3-acetoxymethyl-3-cephem-4-carboxylate, t-butyl 7-chloroacetamido-2-chloromethylidene-3-methyl-3-cephem-4-carboxylate, 2,2,2-trichloroethyl 7-(α-benzyloxycarbonyl-α-phenylacetamido)-2-chloromethylidene-3-acetoxymethyl-3-cephem-4-carboxylate, diphenylmethyl 7-(α-diphenylmethoxycarbonyl-α-phenylacetamido)-2-bromomethylidene-3-methyl-3-cephem-4-carboxylate, and the deesterified free acid forms (formula 1, $R_2$=H), and sulfoxides (formula 1, n=1) thereof.

The esters of the 2-halomethylidene cephalosporins prepared by the above-described process can be deesterified to provide the corresponding free acids. The free acid form of the 7-acyl-2-halomethylidene cephalosporin compounds of the formula 1 wherein n is 0 and $R_2$ is hydrogen are antimicrobial agents which inhibit the growth of microorganisms infectious to man and animals, for example, *Staphylococcus aureus, Sarcina lutea, Bacillus subtilis,* and *Escherichia coli.*

The 2-halomethylidenes of the formula 1 are also useful intermediates in the preparation of 2-aryl (or alkyl) mercaptomethylidene cephalosporins described by Kaiser, et al., *J. Med. Chem.* 14, 426 (1971), as described hereinafter.

The 2-halomethylidene cephalosporins represented by the formula 1 wherein R is hydrogen and n is 0 are 7-amino-2-halomethylidene cephalosporin nucleus compounds. The 7-amino nucleus compounds are prepared by the N-deacylation of a 7-acylamino-2-halomethylidene cephalosporin ester of the formula 1 wherein R is an acyl group

and $R_2$ is a carboxylic acid protecting group. The N-deacylation is carried out by the known N-deacylation process which involves first the preparation of the imino halide with a phosphorus halide, and second the conversion of the imino halide to the corresponding imino ether with an alcohol. Hydrolysis of the imino ether provides the 7-amino nucleus compound. For example, 2,2,2-trichloroethyl 7-phenoxyacetamido-2-chloromethylidene-3-methyl-3-cephem-4-carboxylate is reacted with phosphorus pentachloride in a halogenated hydrocarbon solvent such as methylene chloride in the presence of a tertiary amine such as pyridine or triethylamine at a temperature between about −10° and 20° C. After the imino chloride of the phenoxyacetamido side chain has formed, an alcohol such as methyl alcohol or iso-butyl alcohol is added to the reaction mixture in the cold to form the imino ether. Hydrolysis of the imino ether at about 20° C. provides the 7-amino nucleus which can be isolated in the form of a salt for example, the hydrochloride salt.

The 7-amino-2-halomethylidene cephalosporin nucleus compounds are intermediates for the preparation of 7-acylamido-2-halomethylidene cephalosporins having the desired 7-acyl group of the formula 1. The 7-amino nucleus compounds can be acylated with the desired carboxylic acid derivative by acylation methods well known in the cephalosporin art. For example, the 7-amino nucleus compounds can be acylated with acyl halides in the presence of an acid binding agent or with an active derivative of the carboxylic acid used to form the 7-acyl group. Active derivatives such as acid azides, active esters or anhydrides can be used.

As shown in the above reaction scheme depicting the preparation of the 2-halomethylidene cephalosporins, the sulfoxide group of the starting material is reduced to the sulfide form. The sulfoxide form of the 2-halomethylidene cephalosporin (formula 1, n=1) is prepared by oxidation of the sulfide form by known methods as described hereinafter. The sulfoxides of the formula 1 are useful intermediates in the preparation of 2-acyloxymethylidene substituted cephalosporins as described below.

A preferred group of 2-halomethylidene cephalosporins are represented by the formula 1 wherein R' is $C_1$–$C_4$ alkyl, phenyl, benzyl, phenoxymethyl or thienyl.

Preferred carboxylic acid protecting groups represented by $R_2$ in formula 1 are 2,2,2-trichloroethyl and p-nitrobenzyl.

Especially preferred compounds represented by the formula 1 are p-nitrobenzyl 7-phenoxyacetamido-2-chloromethylidene-3-methyl-3-cephem-4-carboxylate, 2,2,2-trichloroethyl 7-phenoxyacetamido-2-chloromethylidene-3-acetoxymethyl-3-cephem-4-carboxylate, p-nitrobenzyl 7-phenoxyacetamido-2-bromomethylidene-3-methyl-3-cephem-4-carboxylate and the sulfoxide and free acid forms thereof.

A further aspect of the present invention provides 2-hydroxymethylidene cephalosporins and the acyloxy derivatives thereof which are represented by the following structural formula 2.

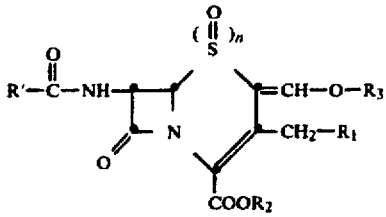

wherein R', $R_1$, $R_2$ and n have the same meanings as defined above for formula 1, and $R_3$ is hydrogen, formyl, $C_2$–$C_4$ alkanoyl or benzoyl.

The term $C_2$–$C_4$ alkanoyl refers to acetyl, propionyl, n-butyryl and iso-butyryl.

In the preparation of a compound of formula 2, a 2-halomethylidene cephalosporin ester of the formula 1 wherein n is 0 is first oxidized to the sulfoxide, and the sulfoxide is reacted with a salt of tetramethylguanidine formed with a $C_1$–$C_4$ alkanoic acid or benzoic acid in an inert solvent to provide the corresponding 2-acyloxymethylidene cephalosporin sulfoxide ester.

The preparation of the 2-acyloxymethylidene compounds of the formula 2 is carried out as follows. The tetramethylguanidinium salt is prepared in an inert solvent and preferably a halogenated hydrocarbon solvent such as methylene chloride, 1,1,2-trichloroethane or tetrachloroethane. Tetramethylguanidine is added to a solution of the $C_1$–$C_4$ alkanoic acid or benzoic acid in the inert solvent. The salt is readily formed at room temperature or in the cold at about 0° C.

The tetramethylguanidinium salt solution is then added dropwise with stirring to a solution or slurry of the 7-acylamido-2-halomethylidene cephalosporin ester sulfoxide in an inert solvent and preferably a halogenated hydrocarbon solvent. The reaction is carried out at a temperature between about 10° C. and about 40° C. and preferably at between about 20° C. and 25° C.

Alternatively, the reaction can be carried out by adding a solution of the 2-halomethylidene cephalosporin ester to the tetramethylguanidinium salt solution.

The 3-acyloxymethylidene sulfoxide ester is recovered as follows. The reaction mixture is washed with water, and brine if desired, and is dried over a suitable drying agent. The dried solution is evaporated to dryness to provide the product in impure form. The sulfoxide form of the product can be purified via chromatography over silica gel or, alternatively, the sulfoxide can be reduced to the sulfide (formula 2, n=0) and the latter purified via chromatography over silica gel.

The reduction of a 3-acyloxymethylidene cephalosporin ester sulfoxide of the formula 2 is carried out by sulfoxide reduction methods known in the cephalosporin art. Preferably, the sulfoxide of the formula 2 is reacted with phosphorus tribromide or phosphorus trichloride in dry dimethylformamide to reduce the sulfoxide to the sulfide form.

The 2-halomethylidene cephalosporin sulfoxide esters of the formula 1 wherein n is 1 are prepared by oxidation of the corresponding sulfide with a peracid. Peracids such as peracetic acid, perbenzoic acid, m-chloroperbenzoic acid or perphthalic acid can be used. m-Chloroperbenzoic acid is preferred.

The 2-hydroxymethylidene cephalosporin sulfoxide ester of the formula 2 wherein $R_3$ is hydrogen is prepared with the 2-formylmethylidene ester by hydrolysis of the formyl group. The hydrolysis is best carried out over silica gel, for example, by stirring a solution of the 2-formyloxymethylidene sulfoxide ester in an inert solvent containing in suspension wet silica gel.

The 2-hydroxymethylidene sulfoxide ester is hydrogen bonded. The 2-hydroxy group forms a hydrogen bond with the sulfoxide of the cephalosporin as shown in the following structural formula.

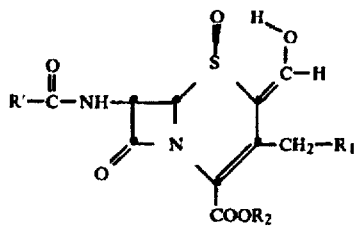

The 2-hydroxymethylidene cephalosporin sulfoxide is useful as an intermediate in the synthesis of the 3-acyloxymethylidene cephalosporins. It is the intermediate in the tranesterification method for preparing the $C_2$–$C_4$ alkanoyloxymethylidene cephalosporins described below.

The 2-hydroxymethylidene cephalosporin in the sulfide form (formula 2, n=0) is prepared by the silica gel hydrolysis of the 2-formyloxymethylidene cephalosporin in the sulfide form (formula 2, $R_3$ is formyl and n=0).

The 2-hydroxymethylidene sulfoxide ester represented by the above formula can be acylated to form the corresponding 2-acyloxymethylidene sulfoxide ester of the above formula 2 wherein $R_3$ is $C_2$–$C_4$ alkanoyl or benzoyl. The esterification of the 2-hydroxymethylidene group can be carried out by reacting a $C_2$–$C_4$ alkanoyl halide or a benzoyl halide, for example, acetyl chloride or acetyl bromide with the 2-hydroxymethylidene ester in the presence of a hydrogen halide acceptor and preferably a tertiary amine such as pyridine or triethylamine in an inert solvent.

The $C_2$–$C_4$ alkanoyloxy methylidene or benzoyloxymethylidene ester of the formula 2, wherein $R_3$ is $C_2$–$C_4$ alkanoyl or benzoyl, are also prepared with the 2-formyloxymethylidene ester by a transesterification reaction. The transesterification occurs during the sulfoxide reduction of a compound of the formula 2 wherein n=1 by following the sulfoxide reduction procedure described by Hatfield in U.S. Pat. No. 4,044,002. Hatfield describes the reduction of cephalosporin sulfoxides which involves the use of an acyl bromide, for example, acetyl bromide, in the presence of a bromine acceptor such as an olefin for example, amylene. In reducing a 2-formyloxymethylidene cephalosporin sulfoxide ester of the formula 2, wherein $R_3$ represents the formyl group and n is 1, under the Hatfield conditions by using a $C_2$–$C_4$ alkanoic acid bromide or benzoyl bromide in the presence of a bromine scavenger such as amylene, transesterification involving the 2-formyl group and the acyl group of the acyl bromide used in the reduction takes place. For example, 2,2,2-trichloroethyl 7-phenoxyacetamido-2-formyloxymethylidene-3-methyl-3-cephem-4-carboxylate sulfoxide is reacted in an inert solvent with acetyl bromide in the presence of amylene to provide 2,2,2-trichloroethyl 7-phenox-yacetamido-2-acetoxymethylidene-3-methyl-3-cephem-4-carboxylate.

The transesterification and sulfoxide reduction reaction involved in the above-described process is illustrated by the following reaction scheme.

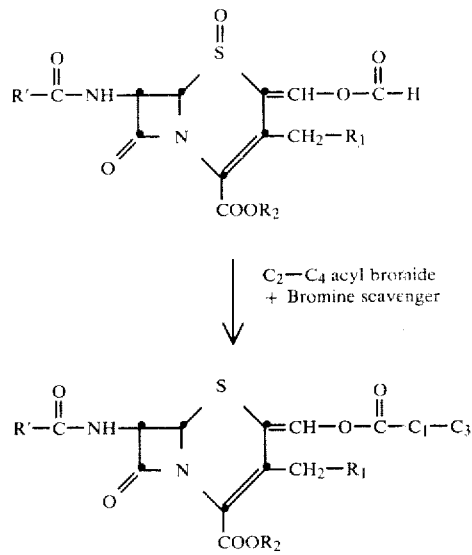

In the above reaction scheme the terms R' and $R_1$ have the same meanings as described above with respect to formula 2, and $R_2$ is a carboxylic acid protecting ester group.

The 2-acyloxymethylidene cephalosporin esters in the sulfide form (formula 2 wherein $R_3$ is $C_2$-$C_4$ alkanoyl, or benzoyl and n is 0), are deesterified to provide the corresponding free acids wherein $R_2$ of the formula 2 is hydrogen. The deesterification of the $R_2$ ester group is carried out by procedures well known in the art, for example, the p-nitrobenzyl ester group can be reductively cleaved by catalytic hydrogenolysis or by treatment with zinc in the presence of acetic acid, the 2,2,2-trichloroethyl ester group can be cleaved by zinc in the presence of an acid, the p-methoxybenzyl ester group can be removed from the molecule by employing trifluoroacetic acid in the presence of anisole, and other ester groups represented by $R_2$ can be cleaved by conventional procedures.

The 2-formyloxymethylidene cephalosporin p-nitrobenzyl esters are deesterified by catalytic hydrogenolysis over palladium on carbon catalyst. On deesterification of the p-nitrobenzyl group with zinc dust and acid, the formate ester group is deesterified. Accordingly, with these formate esters the hydrogenolysis method is preferred.

The free acids of the 2-alkanoyloxymethylidene and 2-benzoyloxymethylidene compounds represented by the formula 2 are antimicrobial agents which inhibit the growth of gram-positive and gram-negative bacteria which are pathogenic to man and animals. For example, in the standard disc-plate assay used for determining antimicrobial activity of cephalosporin compounds, the compound represented by the formula 2 wherein R' is phenoxymethyl, $R_1$ and $R_2$ are hydrogen and $R_3$ is acetyl, demonstrated zones of inhibition against *Bacillus subtilis, Staphylococcus aureus, Sarcina lutea,* and *Escherichia coli.*

The compounds of this invention represented by the formulas 1 and 2, wherein n is 0, $R_2$ is hydrogen, can be used as topical sterilants and in the treatment of infectious diseases in man and animals when administered parenterally. Solutions or emulsions containing the cephalosporin compounds of the formulas 1 and 2 at a concentration between about 1% and about 15% are suitable for topical application. Preferably the compounds of the invention are administered in the salt form. Suitable salts include the sodium and potassium salts or salts formed with pharmaceutically acceptable non-toxic amines such as ammonia or mono- or di-ethanolamine. For parenteral use a suitable salt form of the compound, for example the sodium or potassium salt, can be formulated in unit dosage forms for intramuscular or intravenous administration. Solutions of the salt forms for parenteral use can be made up in physiological fluids such as 5% Dextrose, Water-for-Injection, USP and saline.

As was mentioned previously herein, the 2-halomethylidene cephalosporin sulfoxide esters are converted to 2-arylthiomethylidene cephalosporins and 2-alkylthiomethylidene cephalosporins described by Kaiser, et al., supra. The 2-halomethylidene compounds react with mercaptans to form addition products which are unstable, and which on reaction with a tertiary amine, for example, triethylamine, yield a cis-trans mixture of the 2-alkyl (or aryl) thiomethylidene sulfoxide ester. The addition reaction is illustrated in the following reaction scheme.

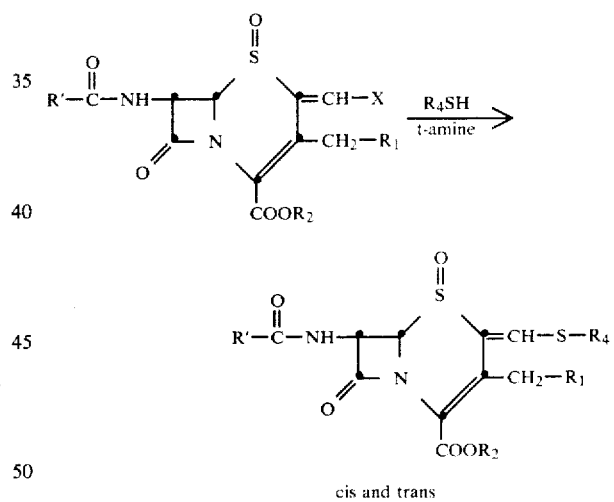

cis and trans

In the above reaction scheme, R', $R_1$, $R_2$ and X have the same meanings as described above with respect to formula 1 and $R_4$ is alkyl, phenyl or substituted phenyl. For example, 2,2,2-trichloroethyl 7-acetamido-2-chloromethylidene-3-methyl-3-cephem-4-carboxylate sulfoxide is reacted with phenylmercaptan in methylene chloride in the presence of triethylamine to provide a mixture of the cis-trans isomer of the corresponding 2-phenylthiomethylidene sulfoxide ester.

The reaction of the 2-halomethylidene sulfoxide ester with the mercaptan is carried out at a temperature between about $-70°$ C. and about $-10°$ C. in an inert solvent and preferably a halogenated hydrocarbon solvent such as methylene chloride. Following the reaction in the cold, the reaction mixture is treated with an acid such as hydrochloric acid and is allowed to warm to about 0° C. The reaction mixture is then washed with water and brine and is dried and evaporated to dryness. The cis and trans isomers are separated and obtained pure by chromatography over a suitable adsorbent and preferably silica gel.

The 2-alkyl (or aryl) thiomethylidene compounds are known antibiotic compounds as described by Kaiser, et al., supra.

Preferred 2-hydroxymethylidene and 2-acyloxymethylidene cephalosporin esters and free acids are represented by the formula 2 wherein R' is $C_1$–$C_4$ alkyl, phenyl, benzyl, phenoxymethyl or thienyl and $R_3$ is formyl or acetyl.

Illustrative 2-hydroxymethylidene and 3-acyloxymethylidene cephalosporins represented by the formula 2 are 2,2,2-trichloroethyl 7-acetamido-2-formyloxymethylidene-3-methyl-3-cephem-4-carboxylate, p-nitrobenzyl 7-phenoxyacetamido-2-formyloxymethylidene-3-acetoxymethyl-3-cephem-4-carboxylate, p-nitrobenzyl 7-phenoxymethylidene-2-hydroxymethylidene-3-acetoxymethyl-3-cephem-4-carboxylate, p-nitrobenzyl 7-phenoxyacetamido-2-acetoxymethylidene-3-acetoxymethyl-3-cephem-4-carboxylate, diphenylmethyl 7-phenylacetamido-2-acetoxymethylidene-3-methyl-3-cephem-4-carboxylate, benzyl 7-(2-furylacetamido)-2-propionoxymethylidene-3-acetoxymethyl-3-cephem-4-carboxylate, p-methoxybenzoyl 7-benzamido-2-benzoyloxymethylidene-3-methyl-3-cephem-4-carboxylate, p-nitrobenzyl 7-(2-thienylacetamido)-2-hydroxymethylidene-3-acetoxymethyl-3-cephem-4-carboxylate, p-nitrobenzyl 7-(2-thienylacetamido)-2-acetoxymethylidene-3-acetoxymethyl-3-cephem-4-carboxylate, 2,2,2-trichloroethyl 7-acetamido-2-hydroxymethylidene-3-methyl-3-cephem-4-carboxylate, diphenylmethyl 7-phenylacetamido-2-hydroxymethylidene-3-acetoxymethyl-3-cephem-4-carboxylate, the sulfoxides and the free acid forms thereof.

An especially preferred 2-acyloxymethylidene cephalosporin of the formula 2 is 2,2,2-trichloroethyl 7-phenoxyacetamido-2-formyloxymethylidene-3-methyl-3-cephem-4-carboxylate and the sulfoxide thereof.

The following examples further illustrate the compounds of the present invention and their method of preparation.

EXAMPLE 1

2,2,2-Trichloroethyl 7-phenoxyacetamido-2-chloromethylidene-3-methyl-3-cephem-4-carboxylate To 100 ml of dimethylformamide (dried over molecular sieve) and cooled briefly in a dry ice-acetone bath were added 1.31 ml (1.5 equiv.) of phosphorus trichloride. The solution was stirred for 30 minutes without cooling while the Vilsmeier reagent (dimethyliminium chloride) was formed. The solution was cooled briefly in a dry ice acetone bath and a solution of 5.08 g of 2,2,2-trichloroethyl 7-phenoxyacetamido-2-exomethylene-3-methyl-3-cephem-4-carboxylate-1-oxide in 30 ml of dry dimethylformamide was added dropwise with stirring. The reaction mixture was stirred for 15 minutes without further cooling and was diluted with ethyl acetate. The solution was washed five times with water, once with saline and once with brine and was dried over sodium sulfate. The dried solution was evaporated to dryness in vacuo and the residue chromatographed over 15 g of silica gel using 900 ml of toluene and 900 ml of 1:1, ethyl acetate:toluene, v:v for elution. Multiple fractions of about 16 ml were collected. Fractions 11–31 were combined and evaporated to dryness. The product, 2,2,2-trichloroethyl 7-phenoxyacetamido-2-chloromethylidene-3-methyl-3-cephem-4-carboxylate, was obtained as 3.86 g of a tan foam. The product was recrystallized from methylene chloride-hexane to give fine white needles melting at about 153° to about 154° C.

Elemental Analysis for $C_{19}H_{16}N_2O_5SCl_4$: Theory: C, 43.37; H, 3.06; N, 5.32; Cl, 26.95. Found: C, 43.65; H, 2.99; N, 5.08; Cl, 27.20.

NMR (CDCl$_3$): δ2.32(s, 3H, CH$_3$), 4.57 (s, 2H, side chain methylene), 4.80, 4.29 (ABq, J=12 Hz, 2H, ester methylene) 5.17 (d, J=5 Hz, 1H, C$_6$H), 5.94 (q, J=5/9 Hz, 1H, C$_7$H) and 6.83 (s, 1H, vinyl H).

EXAMPLE 2 p-Nitrobenzyl 7-phenoxyacetamido-2-chloromethylidene-3-methyl-3-cephem-4-carboxylate To 15 ml of DMF (dried over molecular sieve) and cooled briefly in a dry ice-acetone bath was added 0.131 ml of phosphorus trichloride. The solution was stirred for 20 minutes at room temperature, was then briefly cooled in a dry ice-acetone bath, and a solution of 0.512 g of p-nitrobenzyl 7-phenoxyacetamido-2-exomethylene-3-methyl-3-cephem-4-carboxylate sulfoxide in 20 ml of DMF was added dropwise. The reaction mixture was stirred 20 minutes at room temperature and was transferred to a separatory funnel with cold ethyl acetate. The reaction mixture was washed 5 times with water, 2 times with a saturated sodium chloride solution, was dried over sodium sulfate and evaporated to dryness. The residue was chromatographed over 8.0 g of Merck silica gel using 500 ml of toluene vs 500 ml of ethyl acetate:toluene, 1:1, v:v for elution. There was obtained 0.338 g (63.5%) of the title compound as a froth. The product was obtained as crystalline, fine white needles from methylene chloride-hexane and melted at about 150° C.–151° C.

Elemental Analysis: Theory: C, 54.39; H, 3.80; N, 7.93; Cl, 6.69. Found: C, 54.64; H, 4.02; N, 8.02; Cl, 6.74.

NMR (CDCl$_3$): δ2.29(s, 3H, 3-methyl), 4.52 (s, 2H, phenoxyacetyl methylene), 5.12 (d J=4 Hz, 1H, C$_6$H), 5.34 (s, 2H, ester methylene), 5.90 (q J=4/9 Hz, 1H, C$_7$H), and 6.81 (s, 1H, C$_2$ vinyl H).

IR (CHCl$_3$): β-lactam carbonyl absorption at 1785 cm$^{-1}$.

EXAMPLE 3

2,2,2-Trichloroethyl 7-phenoxyacetamido-2-bromomethylidine-3-methyl-3-cephem-4-carboxylate To 15 ml of DMF briefly cooled in an ice bath were added 0.142 ml of phosphorus tribromide and the solution was stirred for 20 minutes in the cold. A pale yellow solid formed in the solution which was again briefly cooled, and a solution of 0.508 g of 2,2,2-trichloroethyl 7-phenoxyacetamido-2-exomethylene-3-methyl-3-cephem-4-carboxylate sulfoxide in 3 ml of DMF was added dropwise with stirring. The reaction mixture was diluted with ethyl acetate and washed with water and a solution of sodium chloride and was dried and evaporated to dryness. The product was chromatographed over 8.0 g of Merck silica gel using 500 ml of toluene vs 500 ml of ethyl acetate:toluene, 1:1, v:v for elution to give 0.469 g of the product as a brown froth (82%). The product was obtained as crystalline tan needles from methylene chloride-hexane and melted at about 145° C.–146° C.

Elemental Analysis: Theory: C, 39.99; H, 2.83; N, 4.91; Cl, 18.64; Br, 14.00. Found: C, 40.10; H, 3.02; N, 4.97; Cl, 18.90; Br, 14.13.

NMR (CDCl$_3$): δ2.32 (s, 3H, 3-methyl), 4.59 (s, 2H, phenoxyacetyl methylene), 4.68 (d J=5 Hz, 1H, C$_6$H), 4.85, 5.07 (ABq, J=12 Hz, 2H, TCE ester), 6.18 (q, J=5/10 Hz, 1H, C$_7$H), 7.10 (s, 1H, C$_2$ vinyl H), and 7.83 (d, J=10 Hz, 1H, amide NH).

IR (CHCl$_3$): β-lactam carbonyl absorption at 1794 cm$^{-1}$.

EXAMPLE 4

By following the procedures described by Example 3, p-nitrobenzyl 7-phenoxyacetamido-2-exomethylene-3-methyl-3-cephem-4-carboxylate sulfoxide was converted to p-nitrobenzyl 7-phenoxyacetamido-2-bromomethylidene-3-methyl-3-cephem-4-carboxylate which was purified by chromatography by the procedure used to purify the product of Example 3. The product on crystallization from methylene chloride-hexane formed white needles melting at about 151° C. to about 152° C.

Elemental Analysis: Theory: C, 50.18; H, 3.51; N, 7.32. Found: C, 49.94; H, 3.71; N, 7.42.

NMR (CDCl$_3$): δ2.30 (s, 3H, 3-methyl), 4.59 (s, 2H, phenoxyacetyl methylene), 5.12 (d J=4 Hz, 1H, C$_6$H), 5.35 (s, 2H, ester methylene), 5.86 (q J=4/9 Hz, 1H, C$_7$H).

EXAMPLE 5

2,2,2-Trichloroethyl 7-acetamido-2-chloromethylidene-3-methyl-3-cephem-4-carboxylate To 40 ml of DMF cooled in an ice bath were added (0.532 ml of phosphorus trichloride. The solution was stirred with cooling and a solution of 2.127 g of 2,2,2-trichloroethyl 7-acetamido-2-exomethylene-3-methyl-3-cephem-4-carboxylate in 10 ml of DMF was added dropwise. The reaction mixture was stirred with cooling for 10 minutes and was then transferred to a separatory funnel with ethyl acetate and washed with water and a solution of sodium chloride. The mixture was dried over sodium sulfate and evaporated to dryness. The residue was chromatographed over 10 g of Merck silica gel using 600 ml of toluene vs 600 ml of 1:1, ethyl acetate:toluene, v:v. Multiple fractions of about 16 ml were collected. Fractions 7–27 were collected and evaporated to dryness to yield 1.725 g (78.5% yield) of the product. On crystallization from methylene chloride-hexane, the product was obtained crystalline as fine white needles melting at about 176° C. to about 177° C.

Elemental Analysis: Theory: C, 35.97; H, 2.79; N, 6.45; Cl, 32.67. Found: C, 36.17; H, 2.69; N, 6.60; Cl, 32.93.

NMR (CDCl$_3$): δ2.10 (s, 3H, acetamido methyl), 2.33 (s, 3H, 3-methyl), 4.81, 4.99 (AB J=12 Hz, 2H, ester methylene), 5.15 (d J=4 Hz, 1H, C$_6$H), 5.86 (q J=4/9 Hz, 1H, C$_7$H), 6.52 (d J=9 Hz, 1H, amide NH), 6.85 (s, 1H, vinyl H).

IR (CHCl$_3$): β-lactam carbonyl absorption at 1783 cm$^{-1}$.

Mass Spect: 432

UV (ethanol): λmax=323 nm, ε=13,375

The following 2-halomethylidene-3-cephem esters were prepared by the procedures described in the foregoing Examples.

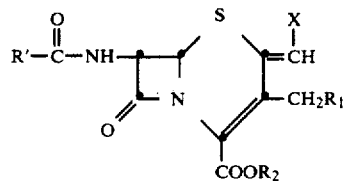

| Ex. No. | R' | R$_1$ | R$_2$ | X |
|---|---|---|---|---|
| 6 | CH$_3$ | H | TCE[1] | Br |
| 7 | 2-thienyl-methyl | O—C(=O)—CH$_3$ | TCE | Cl |
| 8 | 2-thienyl-methyl | " | t-butyl | " |
| 9 | CH$_3$ | H | diphenyl-methyl | Cl |

[1]TCE = 2,2,2-trichloroethyl

The following Examples are preparations of 2-halomethylidene-3-cephem sulfoxide esters.

EXAMPLE 10

2,2,2-Trichloroethyl 7-phenoxyacetamido-2-chloromethylidene-3-methyl-3-cephem-4-carboxylate sulfoxide To a solution of 0.404 g of 2,2,2-trichloroethyl 7-phenoxyacetamido-2-chloromethylidene-3-methyl-3-cephem-4-carboxylate in 40 ml of chloroform cooled to about 5° C. was added dropwise with stirring a solution of 0.173 g (1.1 equivalents) of 85% m-chloroperbenzoic acid in about 3 ml of chloroform. After 5 minutes the reaction mixture was washed once with a solution of sodium bicarbonate, once with water and once with a solution of sodium chloride and was dried. The dried solution was evaporated to dryness and the residue of product was chromatographed over 8 g of Merck silica gel using 500 ml of toluene vs. 500 ml of 1:1 ethyl acetate:toluene, v:v. Multiple fractions of 16 ml were collected. Fractions 17–23 were combined and evaporated to dryness and yielded 1.343 g (82% yield) of the sulfoxide product as one isomer. The sulfoxide was crystallized as white needles from methylene chloride-hexane and melted at about 170° C. to 171° C. with decomposition.

Elemental Analysis:

Theory: C, 42.09; H, 2.97; N, 5.17; O, 26.15. Found: C, 42.19; H, 3.22; N, 5.15; O, 26.41.

IR (CHCl$_3$): β-lactam carbonyl absorption at 1808 cm$^{-1}$.

NMR (100 MC, CDCl$_3$): δ2.34 (s, 3H, 3-methyl), 4.58 (s, 2H, phenoxyacetyl methylene), 4.82, 4.91 (AB J=12 Hz, 2H, ester methylene), 5.21 (d, J=Hz, 1H, C$_6$H), 5.95 (q J=4/9 Hz, 1H, C$_7$), 7.09 (s, 1H, vinyl H).

By following the procedure of Example 10 the following 2-halomethylidene 3-cephem sulfoxide esters were obtained.

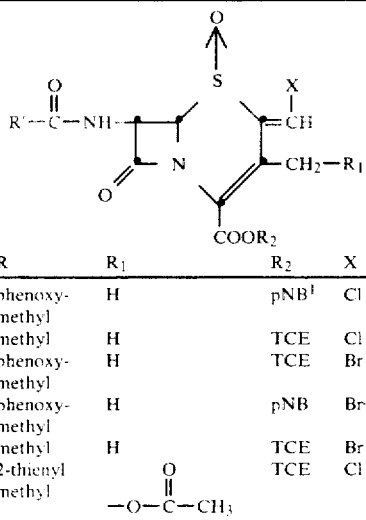

| Ex. No. | R | R₁ | R₂ | X | mp. °C. |
|---|---|---|---|---|---|
| 11 | phenoxymethyl | H | pNB[1] | Cl | 230 d |
| 12 | methyl | H | TCE | Cl | — |
| 13 | phenoxymethyl | H | TCE | Br | 177–178 |
| 14 | phenoxymethyl | H | pNB | Br | 195 |
| 15 | methyl | H | TCE | Br | 204 d |
| 16 | 2-thienylmethyl | —O—C(=O)—CH₃ | TCE | Cl | — |

[1] pNB = p-nitrobenzyl

The following Examples describe preparations of 2-alkanoyloxymethylidene-3-cephem esters and free acids.

EXAMPLE 17

2,2,2-Trichloroethyl 7-acetamido-2-formyloxymethylidene-3-methyl-3-cephem-4-carboxylate A solution of tetramethylguanidinium formate in methylene chloride was prepared by combining at room temperature 0.064 g of formic acid with 0.159 g of tetramethylguanidine in 15 ml of methylene chloride. The solution was stirred at room temperature for 5 minutes and a solution of 0.311 g., 1 eq., of 2,2,2-trichloroethyl 7-acetamido-2-chloromethylidene-3-methyl-3-cephem-4-carboxylate sulfoxide in about 25 ml of methylene chloride was added. The reaction mixture was stirred at room temperature for 5 minutes during which time the color of the solution changed from yellow to brown. The reaction mixture was washed with water and an aqueous solution of sodium chloride, was dried, and evaporated to dryness. The 2-formyloxymethylidene ester sulfoxide was obtained as a yellow froth weighing 0.308 g (97% yield).

The sulfoxide group of the product was reduced as follows. The sulfoxide ester, 0.308 g, was dissolved in 10 ml of DMF and the solution treated with 0.130 ml (2 eq.) of phosphorus tribromide. The reduction mixture was allowed to react 5 minutes and was then washed twice with water and once with an aqueous sodium chloride solution, dried and evaporated to dryness. The product was obtained as 0.246 g of a brown gum. The product was chromatographed over 6 g of Merck silica gel using 500 ml of 25% ethyl acetate in toluene vs. 500 ml of 25% acetone in ethyl acetate. There were obtained 16 mg of purified 2,2,2-trichloroethyl 7-acetamido-2-formyloxymethylidene-3-methyl-3-cephem-4-carboxylate.

IR (CHCl₃): β-lactam carbonyl absorption at 1785 cm⁻¹

NMR (T60, CDCl₃): δ2.17 (s, 3H, acetyl methyl), 2.60 (s, 3H, 3-methyl), 4.9 (s, 2H, ester methylene), 5.52 5.52 (d J=4 Hz, 1H, C₆H), 5.80 (q J=4/8 Hz, C₇H), 8.05 (s, 1H, vinyl H), and 10.3 (s, 1H, formyl ester H).

EXAMPLE 18

7-Phenoxyacetamido-2-acetoxymethylidene-3-methyl-3-cephem-4-carboxylic acid

To a solution of 0.535 ml of formic acid in about 15 ml of methylene chloride cooled to 5° C. were added with stirring 1.78 ml of tetramethylguanidine. The solution was allowed to stir at room temperature for 5 minutes to complete formation of tetramethylguanidinium formate. The solution was then added dropwise with stirring to a slurry of 4.19 g of p-nitrobenzyl 7-phenoxyacetamido-2-bromomethylidene-3-methyl-3-cephem-4-carboxylate sulfoxide in 80 ml of methylene chloride. The solution which formed immediately was stirred at room temperature for 5 minutes to allow for formation of the intermediate 2-formyloxymethylidene ester sulfoxide.

The reaction mixture was then treated with 3.0 ml of amylene and 2.3 ml of acetyl bromide and the solution stirred at room temperature for 20 minutes. The reaction mixture was washed twice with water in the cold, twice with an aqueous solution of sodium chloride and was dried and evaporated to dryness. The residue was chromatographed on 20 g of Merck silica gel using 1 liter of toluene vs. 1 liter of 70% ethyl acetatetoluene by volume. There was obtained 3.058 g (78% yield) of p-nitrobenzyl 7-phenoxyacetamido-2-acetoxymethylidene-3-methyl-3-cephem-4-carboxylate.

IR (CHCl₃): β-lactam carbonyl at 1778 cm⁻¹.

UV (90% ethyl alcohol): λmax 268, 313 nm NMR (100 mc, CDCl₃): δ2.22, 2.25, 3.01, 4.44 (m, 6H, 3-methyl and acetoxy methyl), 4.59 (s, 2H, phenoxy acetyl methylene), 5.08 (d J=4 Hz, 1H, C₆H), 5.37 (s, 2H, ester methylene), 5.89 (q J=4/9 Hz, 1H, C₇H), and 7.94 (s, 1H, vinyl H).

The 2-acetoxymethylidene ester, 0.458 g, was dissolved in about 2 ml of methylene chloride and 50 ml of methyl alcohol and a little additional methylene chloride were added. The solution was added to a prereduced suspension of 0.458 g of 5% palladium on carbon in 30 ml of ethyl alcohol and the mixture hydrogenated for 2 hours under 46 psi. hydrogen pressure. After the catalyst was filtered the pale yellow filtrate was evaporated to dryness. The residue of product was redissolved in methylene chloride and the solution refiltered. The filtrate was evaporated to dryness yielding 0.349 g of the deesterified product. The product was dissolved in cold ethyl acetate and extracted twice with cold aqueous solutions of sodium bicarbonate. The aqueous extracts were combined, layered with cold ethyl acetate, and acidified with cold 1 N hydrochloric acid. The ethyl acetate layer was separated, washed with an aqueous solution of sodium chloride, dried and evaporated to dryness. There was obtained 0.273 g (79% yield) of 7-phenoxyacetamido-2-acetoxymethylidene-3-methyl-3-cephem-4-carboxylic acid as a pale yellow solid.

NMR (T-60, CDCl₃): δ2.2 (m, 6H, 3-methyl, acetoxy methyl), 4.59 (s, 2H, phenoxyacetyl methylene), 5.02 (d J=4 Hz, 1H, C₆H), 5.82 (q J=4/8 Hz, 1H, C₇H).

UV (90% ethyl alcohol): λmax 308 nm

EXAMPLE 19

2,2,2-Trichloroethyl 7-acetamido-2-acetoxymethylidene-3-methyl-3-cephem-4-carboxylate By following the procedures described by Example 18, 0.450 g of 2,2,2-trichloroethyl 7-acetamido-2-chloromethylidene-3-methyl-3-cephem-4-carboxylate sulfoxide were converted to the intermediate 2-formyloxymethylidene sulfoxide ester with 2 equivalents of tetramethylguanidinium formate, and the intermediate reacted with acetyl bromide in the presence of amylene. There were obtained 0.202 g (36% yield) of the purified title compound following chromatography over 10 g Merck silica gel using 500 ml of toluene vs. 500 ml of 1:1, ethyl acetate:toluene, v:v.

IR (CHCl$_3$): β-lactam carbonyl at 1776 cm$^{-1}$

NMR (T-60, CDCl$_3$): δ2.0–2.4 (m, 9H, 3-methyl, acetoxy and acetamido), 4.90 (AB, 2H, ester methylene) 5.05 (d J=4 Hz, 1H, C$_6$H), 5.82 (q J=4/9 Hz, 1H, C$_7$H), 7.95 (s, 1H, vinyl H).

EXAMPLE 20

By following the procedures described by Example 18, and substituting trichloroacetyl bromide for acetyl bromide in the sulfoxide reduction, there is obtained 7-phenoxyacetamido-2-trichloroacetoxymethylidene-3-methyl-3-cephem-4-carboxylic acid.

EXAMPLE 21

By following the procedures of Example 18, and substituting propionyl bromide for acetyl bromide in the sulfoxide reduction, there is obtained 7-phenoxyacetamido-2-propionyloxymethylidene-3-methyl-3-cephem-4-carboxylic acid.

EXAMPLE 22

By following the procedures described by Example 17, the following 2-formyloxymethylidene esters are prepared:

p-methoxybenzyl 7-phenylacetamido-2-formyloxymethylidene-3-acetoxymethyl-3-cephem-4-carboxylate, diphenylmethyl 7-(2-furylacetamido)-2-formyloxymethylidene-3-acetoxymethyl-3-cephem-4-carboxylate, t-butyl 7-(2-thienylacetamido)-2-formyloxymethylidene-3-acetoxymethyl-3-cephem-4-carboxylate, and p-nitrobenzyl 7-(2-thienylacetamido)-2-formyloxymethylidene-3-acetoxymethyl-3-cephem-4-carboxylate.

EXAMPLE 23

This Example is illustrative of the preparation of 2-arylmercaptomethylidene- and 2-alkylmercaptomethylidene-3-cephem esters with 2-halomethylidene sulfoxide esters, 2,2,2-trichloroethyl 7-acetamido-2-phenylmercaptomethylidene-3-methyl-3-cephem-4-carboxylate sulfoxide.

To a solution of 0.285 ml (2.25 equiv.) of benzenethiol and 0.400 ml (2.25 equiv.) of triethylamine in 15 ml of methylene chloride maintained at −68° C. was added dropwise with stirring a solution of 0.557 g of 2,2,2-trichloroethyl 7-acetamido-2-chloromethylidene-3-methyl-3-cephem-4-carboxylate sulfoxide in 10 ml of methylene chloride. The reaction mixture was stirred for 10 minutes while the temperature rose to −10° C. The reaction mixture was treated with 1 N hydrochloric acid and was warmed to 0° C. The mixture was then washed with water and an aqueous solution of sodium chloride, was dried and evaporated to dryness. The residue was chromatographed over 8 g of Merck silica gel using 500 ml of toluene vs. 500 liters of 1:1, ethyl ethyl acetate:toluene, v:v. Multiple 16 ml fractions were collected. Fractions 24–30 gave 0.221 g of isomer I as a yellow solid which on crystallization from methylene chloride-hexane melted at about 198° C. to about 199° C. d. Fractions 33–39 gave 0.124 g of isomer II as a yellow solid which on crystallization from the same solvent mixture melted at about 208° C. to about 209° C. d.

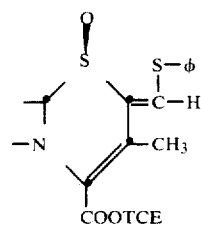

Isomer I

Elemental Analysis: Theory: C, 43.56; H, 3.27; N, 5.35. Found: C, 43.77; H, 3.50; N, 5.26.

UV (90% ethyl alcohol): λmax 348 ε23,780.

NMR (100 mc, CDCl$_3$): δ2.10 (s, 3H, acetamido), 2.32 (s, 3H, 3-methyl), 4.72 (d J=4 Hz, 1H, C$_6$H), 4.83, 5.06 (AB J=12 Hz, 2H, ester methylene), 6.13 (q J=4/10 Hz, 1H, C$_7$H), 7.47 (s, 5H, phenyl), 7.51 (s, 1H, vinyl H).

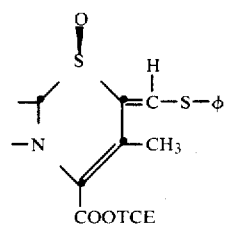

Isomer II

NMR (100 mc, CDCl$_3$): δ2.06 (s, 3H, acetamido), 2.06 (s, 3H, 3-methyl), 4.64 (d J=4 Hz, 1H, C$_6$H), 4.83, 5.09 (ABJ=12 Hz, 2H, ester methylene), 6.09 (q J=4/10 Hz, 1H, C$_7$H), 6.71 (d J=10 Hz, 1H, NH), 7.47 (s, 6H, phenyl and vinyl H).

I claim:

1. A compound of the formula

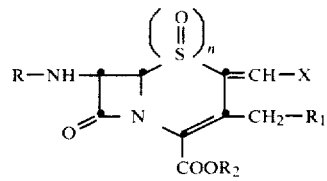

wherein R is hydrogen;
R$_1$ is hydrogen or acetoxy;
X is chloro or bromo;
R$_2$ is hydrogen or a carboxylic acid protecting group; and n is 0 or 1.

* * * * *